(12) United States Patent
Zumbrum et al.

(10) Patent No.: US 9,975,753 B1
(45) Date of Patent: May 22, 2018

(54) DETACHABLE FLUID TRANSFER DEVICE ACCESSORY AND A FLUID TRANSFER ASSEMBLY

(71) Applicant: Allpure Technologies, LLC, New Oxford, PA (US)

(72) Inventors: Michael A Zumbrum, New Oxford, PA (US); Kevin M Perdue, Havre de Grace, MD (US)

(73) Assignee: Sartorius Stedim North America Inc., Bohemia, NY (US)

( * ) Notice: Subject to any disclaimer, the term of this patent is extended or adjusted under 35 U.S.C. 154(b) by 0 days. days.

(21) Appl. No.: 15/498,091

(22) Filed: Apr. 26, 2017

(51) Int. Cl.
  *B65B 1/04* (2006.01)
  *B67D 7/02* (2010.01)
  *B67D 7/78* (2010.01)

(52) U.S. Cl.
  CPC ............. *B67D 7/0288* (2013.01); *B67D 7/78* (2013.01)

(58) Field of Classification Search
  CPC ................................ B67D 7/0288; B67D 7/78
  See application file for complete search history.

(56) References Cited

U.S. PATENT DOCUMENTS

| | | |
|---|---|---|
| 2,685,412 A | 8/1954 | Schell |
| 2,767,587 A | 10/1956 | Perkins |
| 2,859,932 A | 11/1958 | Mackal |
| 2,872,817 A | 2/1959 | Pitts |
| 2,994,224 A | 8/1961 | Brown |
| 3,276,447 A | 10/1966 | Hamilton et al. |
| 3,736,099 A | 5/1973 | Begg et al. |
| 3,776,042 A | 12/1973 | Werra et al. |
| 3,779,082 A | 12/1973 | Galloway |
| 3,858,449 A | 1/1975 | Singer |
| 4,018,059 A | 4/1977 | Hatch |
| 4,056,981 A | 11/1977 | Kalka et al. |
| 4,244,224 A | 1/1981 | Conn |

(Continued)

FOREIGN PATENT DOCUMENTS

| | | |
|---|---|---|
| DE | 2161702 | 6/1973 |
| DE | 3633431 | 4/1988 |

(Continued)

OTHER PUBLICATIONS

Lynx ST Connectors. Datasheet [online], Millipore Corporation, 2008. Retrieved from the Internet: www.millipore.com (4 pages).

(Continued)

*Primary Examiner* — Jason K Niesz
(74) *Attorney, Agent, or Firm* — Womble Bond Dickinson (US) LLP

(57) ABSTRACT

Detachable fluid transfer device accessories and fluid transfer assemblies are provided. The device accessories can include an upper extension defining a lower engagement surface; a lower extension defining an upwardly extending protrusion; a connector portion extending between the upper extension and the lower extension; and a resilient engagement member coupled to the lower engagement surface of the body. The upper extension, the lower extension, and the connector portion can collectively define a cavity configured to receive a tab assembly of a fluid transfer device, where the upwardly extending protrusion is configured to engage a housing of the fluid transfer device, and the resilient engagement member is configured to engage an upper surface of the tab assembly to retain the tab assembly in a fixed configuration relative to the housing.

20 Claims, 8 Drawing Sheets

(56) References Cited

U.S. PATENT DOCUMENTS

| | | | |
|---|---|---|---|
| 4,296,759 | A | 10/1981 | Joslin et al. |
| 4,479,393 | A | 10/1984 | Shores |
| 4,525,127 | A | 6/1985 | Welker |
| 4,527,436 | A | 7/1985 | Jones |
| 4,537,593 | A | 8/1985 | Alchas |
| 4,541,457 | A | 9/1985 | Blenkush et al. |
| 4,557,151 | A | 12/1985 | Welker |
| 4,569,236 | A | 2/1986 | Kitchen et al. |
| 4,587,856 | A | 5/1986 | Otis |
| 4,622,457 | A | 11/1986 | Bradley et al. |
| 4,669,321 | A | 6/1987 | Meyer |
| 4,848,725 | A | 7/1989 | Tibbals, Jr. |
| 4,861,239 | A | 8/1989 | Simmons et al. |
| 4,941,517 | A | 7/1990 | Galloway |
| 5,031,841 | A | 7/1991 | Schafer |
| 5,158,558 | A | 10/1992 | Melker et al. |
| 5,246,204 | A | 9/1993 | Ottung |
| 5,360,413 | A | 11/1994 | Leason et al. |
| 5,463,908 | A | 11/1995 | Rosolia |
| 5,474,546 | A | 12/1995 | Ambrisco et al. |
| 5,535,635 | A | 7/1996 | Shaw |
| 5,839,715 | A | 11/1998 | Leinsing |
| 5,868,433 | A | 2/1999 | Matkovich et al. |
| 6,032,543 | A | 3/2000 | Arthun et al. |
| 6,145,810 | A | 11/2000 | Connoly et al. |
| 6,221,041 | B1 | 4/2001 | Russo |
| 6,234,122 | B1 | 5/2001 | Kirshbaum et al. |
| 6,290,265 | B1 | 9/2001 | Warburton-Pitt et al. |
| 6,516,677 | B1 | 2/2003 | Suter |
| 6,558,365 | B2 | 5/2003 | Zinger et al. |
| 6,699,229 | B2 | 3/2004 | Zinger et al. |
| 6,715,624 | B2 | 4/2004 | Brockwell |
| 6,916,012 | B2 | 7/2005 | Newberg et al. |
| 6,994,315 | B2 | 2/2006 | Ryan et al. |
| 7,272,981 | B2 | 9/2007 | Bigalke |
| 7,293,475 | B2 | 11/2007 | Furey et al. |
| 7,293,477 | B2 | 11/2007 | Furey et al. |
| 7,350,535 | B2 | 4/2008 | Liepold et al. |
| 7,407,612 | B2 | 8/2008 | Warburton-Pitt et al. |
| 7,578,205 | B2 | 8/2009 | Belongia et al. |
| 7,647,861 | B2 | 1/2010 | Bessman |
| 7,927,316 | B2 | 4/2011 | Prouix et al. |
| 8,408,078 | B2 | 4/2013 | Mennenga et al. |
| 8,505,396 | B2 | 8/2013 | Zumbrum |
| 8,544,349 | B2 | 10/2013 | Zumbrum |
| 8,562,572 | B2 | 10/2013 | Prouix et al. |
| 8,579,871 | B2 | 11/2013 | Prouix et al. |
| 8,613,422 | B2 | 12/2013 | Zumbrum |
| 9,028,779 | B2 | 5/2015 | Olivier |
| 9,259,563 | B2 | 2/2016 | Klingel, Jr. et al. |
| 9,568,113 | B2 | 2/2017 | Zumbrum |
| 2006/0065868 | A1 | 3/2006 | Strong |
| 2007/0193375 | A1 | 8/2007 | Pandori et al. |

FOREIGN PATENT DOCUMENTS

| | | |
|---|---|---|
| DE | 3701250 | 7/1988 |
| DE | 69807924 | 1/2003 |
| EP | 0103396 | 3/1984 |
| EP | 0858589 | 8/1998 |
| EP | 1329210 | 7/2003 |
| JP | 2001523525 | 11/2001 |
| SE | 507448 | 6/1998 |
| SU | 649954 | 2/1979 |
| WO | WO 86/02450 | 4/1986 |
| WO | WO 91/00215 | 1/1991 |
| WO | WO 97/16715 | 5/1997 |
| WO | WO 99/26580 | 6/1999 |
| WO | WO 03/90843 | 11/2003 |
| WO | WO 2008-042285 | 4/2008 |
| WO | WO 2008-136720 | 11/2008 |
| WO | WO 2010/008395 | 1/2010 |
| WO | WO 2010/008396 | 1/2010 |
| WO | WO 2011088350 | 11/2011 |

OTHER PUBLICATIONS

Guidelines for Using the Lynx ST Connector. Technical Brief [online], Millipore Corporation, 2008. Retrieved from the Internet: www.millipore.com (2 pages).

FluidLine Technology Corporation FLT Bleed/ Sample Valve Maintenance, Nov. 10, 2008. Datasheet [online], Fluid Line Technology. Retrieved from the Internet: www.fluidlinetech.com (1 page).

Risk Free Connection of Sterilized Single-Use Fluid Path Assemblies to Stainless Steel SIP Systems with Lynx ST (Steam-To) Connectors [online], Millipore Corporation, 2008. Retrieved from the Internet: www.millipore.com (8 pages).

Pure-Flo Solutions, Pure-Flo Radial Seated Tank Bottom Diaphragm Valve. Datasheet [online], ITT Industries, 2001. (2 pages).

ITT Sample & Bleed Valves. Datasheet [online], ITT Corporation, 2006. Retrieved from the Internet: www.ittpureflo.com (4 pages).

Greene, R. and R. D'Aquino, "Disposable equipment: A mainstay in bioprocessing", Chemical Engineering Progress, pp. 10-11, Nov. 1, 2002.

Haughney, H. and H. Aranha, "Disposable processing gains you a competitive edge: enhancing manufacturing capacity with disposable filters, connectors, and membrane chromatography", Biopharm International, p. 50, Oct. 2003.

Haughney, H. and M. Cardona, "Taking disposable processing to the next level: a recent innovation extends the cost, labor and safety benefits of disposable processing to critical clarification and prefiltration steps used in pharmaceutical manufacturing", Biopharm. Trends, pp. 20-22, Jun. 2004.

Janetschek, R., "Capsule Filters & Disposable Sterile Processing Systems," Pharmaceutical Processing, p. 8, Jan. 2001.

Tingley, S., "Plastic factory: disposable biopharmaceutical manufacturing takes a giant leap forward; disposable technologies are quickly beginning to change the face of pharmaceutical cleanroom facility design and economics." Alternative Manufacturing. (part one of two in series) (related article: Identified Causes of Aseptic Processing Failures), Clean Rooms, pp. 1-4, Feb. 2003.

Tingly, S.; "Plastic Factory, Part II: The final pieces of the disposable puzzle. Alternative Manufacturing. Sterile transfer process systems." Clean Rooms, pp. 1-3, Jun. 2003.

Wendt, D.; "Disposable processing systems: how suppliers are meeting today's biotech challenges from fluid handling to filtration." Biopharm International, p. 18, Jul. 2003.

"New quality of data for bioprocessing bags. (Application Area)" Pharmaceutical Processing. Retrieved from the Internet: <URL: http://www.accessmylibrary.com/coms2/summary_0286-25022745_ITM> pp. 1-2, Jan. 2002.

"Connecting the Sanitary Flange", Datasheet [online], Millipore Corporation, pp. 1-2, 2007. E.

International Application Published Under the Patent Cooperation Treaty with International Search Report, PCT/US2008/070482, WO 2010/008395, published Jan. 21, 2010.

International Application Published Under the Patent Cooperation Treaty with International Search Report, PCT/US2008/070488, WO 2010/008396, published Jan. 21, 2010.

Written Opinion of the International Searching Authority, Application No. PCT/US2008/070482, filed Jul. 18, 2008, dated Apr. 16, 2009.

ITT Dualrange Control Valve. Datasheet [online], Pure-Flo. Retrieved from the Internet: www.ittpureflo.com (2 pages); date unknown, believed to be at least as early as Jul. 18, 2008.

Sanitary Inline Bleed and Sample Valves. Datasheet [online], Fluid Line Technology. Retrieved from the Internet: www.fluidlinetech.com (1 page); date unknown, believed to be at least as early as Jul. 18, 2008.

Colder Products—Quick Couplings and Fittings for Industrial Applications—Industrial Products. Retrieved from the Internet: <URL: http://www.colder.com/Markets/Industrial/IndustrialProducts/tabid/821/Default.aspx?ProductID=23> (1 page); date unknown, believed to be at least as early as Jul. 18, 2008.

Sanitary Inline Bleed and Sample Valves. Datasheet [online], Fluid Line Technology, Retrieved from the Internet: www.fluidlinetech.com (1 page); date unknown, believed to be at least as early as Jul. 18, 2008.

(56) References Cited

OTHER PUBLICATIONS

Casella Sales & Marketing Inc., CSMI Sample Valves, Datasheet [online]. Retrieved from the Internet: www.casellasales.com (2 pages); date unknown, believed to be at least as early as Jul. 18, 2008.

"Rapid Aseptic Fluid Transfer System Introduction" Stedim Biosystems, [online]. Retrieved from the Internet: <URL: http://www.stedim.com/p2A_IDC_introduction.php> (2 pages); date unknown, believed to be at least as early as Jul. 18, 2008.

"Gore's Preliminary Invalidity Contentions to Plaintiff Millipore Corporation", (*Millipore Corporation* v. *W.L. Gore & Associates, Inc.*; Civil Action No. 09-10765 DPW) (108 pages). Oct. 29, 2009.

"Sip-Able Sample Valve", Datasheet [online]. Retrieved from the Internet: www.fluidlinetech.com (1 page); date unknown, believed to be at least as early as Jul. 18, 2008.

International Application Published under the Patent Cooperation Treaty with International Search Report, PCT/US2011/021341 (PCT application published as WO-2011/088350 A2) published Jul. 21, 2011.

DETACHABLE FLUID TRANSFER DEVICE ACCESSORY AND A FLUID TRANSFER ASSEMBLY

TECHNICAL FIELD

This disclosure relates generally to a device accessory for a fluid transfer assembly that allows for the transfer of fluids and, more specifically, to a detachable fluid transfer device accessory for detachable use in a fluid transfer assembly that allows for the transfer of fluid through the assembly to multiple fluid vessels.

BACKGROUND

In the manufacturing and processing of many different products, it often is necessary to transfer fluid into or out of a closed processing system and do so in a substantially aseptic, hygienic, or sterile manner. In particular, the need to transfer fluid often arises in the manufacturing and processing of pharmaceuticals, biopharmaceuticals, or other biotechnology applications where processes are conducted in large process tanks, including but not limited to, the transfer of media solutions. The need for fluid transfer arises in other applications and industries as well, including but not limited to, the production of food, cosmetics, paint, chemicals, including hazardous chemicals, and the transfer and handling of semiconductor fluids. During transfers or sampling, fluid in tanks or other vessels must remain substantially free of contaminants. In addition, when making such transfers, it is desirable to keep the environment surrounding a vessel free from contamination by the contents of the vessel or a sample taken therefrom. It is often the case that throughout the manufacturing process there is a need to take multiple samples from the fluid or, in some circumstances, add additional fluid or media to the fluid in a vessel. To accomplish a substantially aseptic, hygienic, or sterile transfer, it is desirable to control the environment through which the fluid flows, for example, the pathway from a tank to a sample container should be substantially aseptic, hygienic, or sterile along the entire pathway. Furthermore, it is desirable that the fluid transfer device be safe for use, reliable, and of low-cost construction.

It is also desirable to transfer fluid using a device which is pre-sterilized and disposable. A pre-sterilized device avoids the need for an operator to prepare the device for use. In addition, a disposable device avoids the time consuming and laborious task of sterilizing sampling equipment.

In view of the above, there exists a need for a detachable fluid transfer device accessory for a fluid transfer device that is pre-sterilized and disposable and capable of use in common industrial settings, such as those found in the pharmaceutical, biopharmaceutical, or other high purity industries.

SUMMARY

Briefly described, there is a detachable fluid transfer device accessory, comprising: a body, comprising: an upper extension defining a lower engagement surface; a lower extension defining an upwardly extending protrusion; and a connector portion extending between the upper extension and the lower extension; and a resilient engagement member coupled to the lower engagement surface of the body, the upper extension, the lower extension, and the connector portion collectively defining a cavity configured to receive a tab assembly of a fluid transfer device, the upwardly extending protrusion being configured to engage a housing of the fluid transfer device, the resilient engagement member being configured to engage an upper surface of the tab assembly to retain the tab assembly in a fixed configuration relative to the housing.

In another embodiment, there is disclosed a fluid transfer assembly, comprising: a fluid transfer device, comprising: a plurality of tab assemblies; a housing defining a plurality of chambers respectively receiving one of the tab assemblies, each of the tab assemblies being moveable with respect to the housing between an extended configuration and a depressed configuration, the depressed configuration allowing flow of a fluid through the fluid transfer device; and a detachable fluid transfer device accessory configured to releasably clamp one or more of the tab assemblies and the housing to retain the one or more of the tab assemblies in the depressed configuration.

Thus, a detachable fluid transfer device accessory and a fluid transfer assembly are disclosed that possess distinct attributes and represent distinct improvements. These and other aspects, features, and advantages of the detachable fluid transfer device accessories and the fluid transfer assemblies of this disclosure will be better understood and appreciated upon review of the detailed description set forth below when taken in conjunction with the accompanying drawing figures, described briefly below. According to common practice, the various features of the drawings may not be drawn to scale. Dimensions and relative sizes of various features and elements in the drawings may be shown enlarged or reduced to illustrate more clearly the embodiments of the invention.

These and other features, aspects, and advantages of the present disclosure will be apparent from a reading of the following detailed description together with the accompanying drawings, which are briefly described below. The present disclosure includes any combination of two, three, four, or more features or elements set forth in this disclosure or recited in any one or more of the claims, regardless of whether such features or elements are expressly combined or otherwise recited in a specific embodiment description or claim herein. This disclosure is intended to be read holistically such that any separable features or elements of the disclosure, in any of its aspects and embodiments, should be viewed as intended, to be combinable, unless the context of the disclosure clearly dictates otherwise.

DETAILED DESCRIPTION OF PREFERRED EMBODIMENTS

Figure 1:
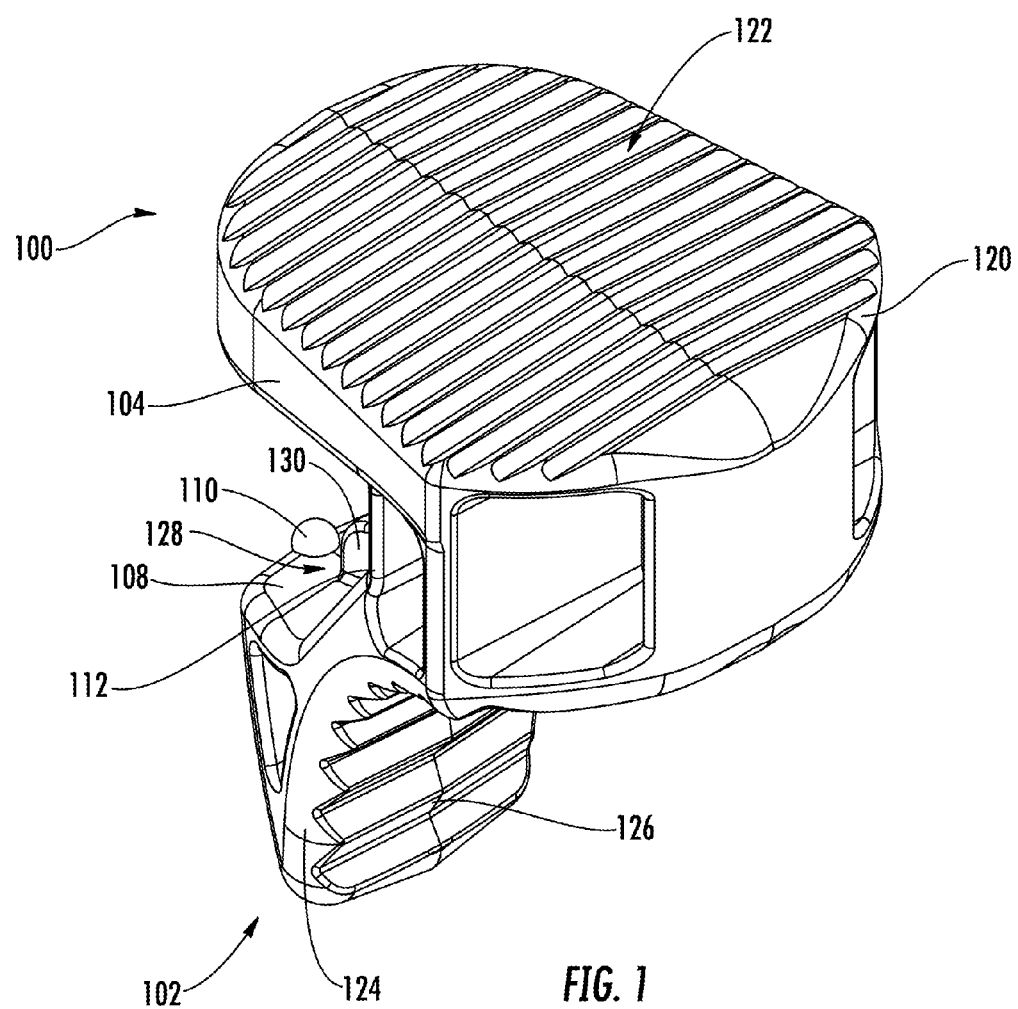
FIG. 1 is a top perspective view of a fluid transfer device accessory.
Figure 2:
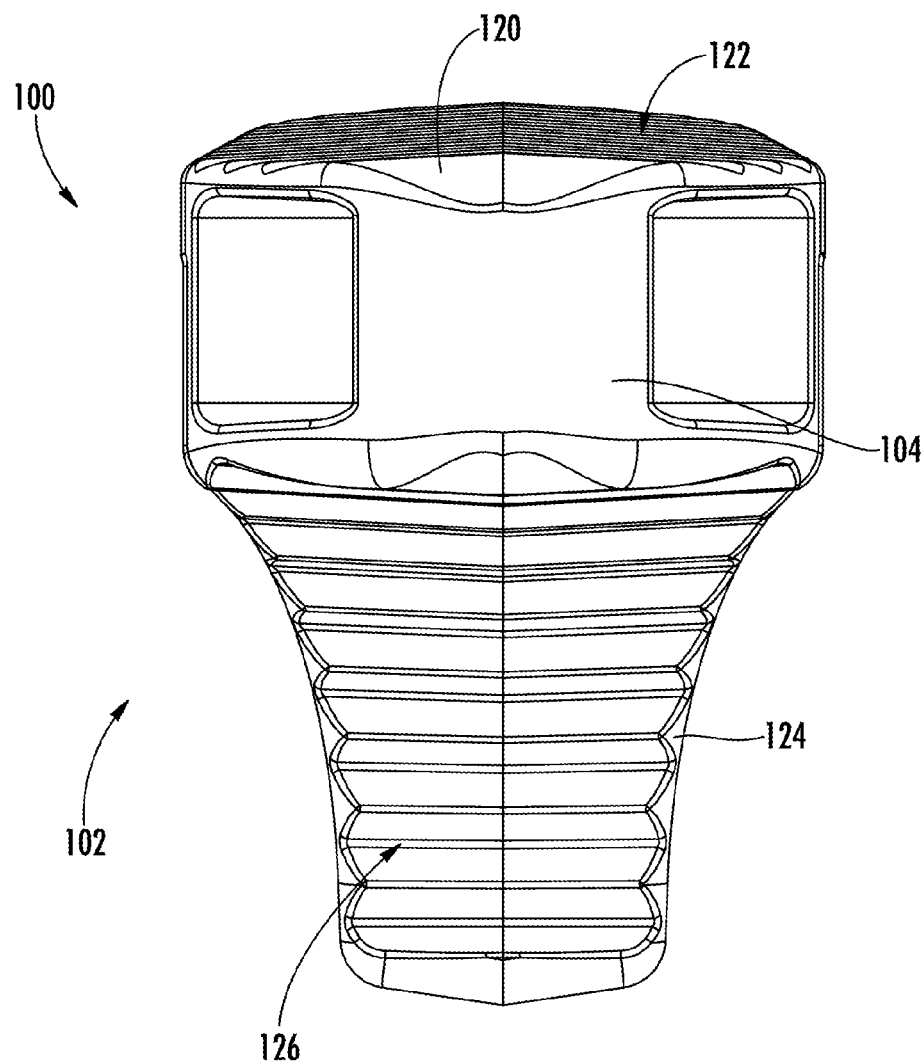
FIG. 2 is a front view of the fluid transfer device accessory of FIG. 1.

Certain exemplary embodiments of the present invention are described below and illustrated in the accompanying figures. The embodiments described are only for purposes of illustrating the present invention and should not be interpreted as limiting the scope of the invention, which, of course, is limited only by the claims below. Other embodiments of the invention, and certain modifications and improvements of the described embodiments, will occur to those skilled in the art, and all such alternate embodiments, modifications, and improvements are within the scope of the present invention.

In some aspects, a fluid transfer assembly is used for distribution of fluid between large and small vessels. For example, a fluid transfer assembly may be useful for sampling a small volume off of a line or body when transferring from one vessel to another vessel, whether or not those vessels are of the same size. In another example, a fluid transfer assembly may be useful for adding one or more fluids from one vessel into another vessel (e.g., a small size vessel into a larger size vessel). In a further example, a fluid transfer assembly may be useful for incorporating into vessel closures (e.g., MYCAP™) for the addition or removal of one, two, three, four, etc., fluids within the same vessel.

Referring now in more detail to the drawing figures, wherein like reference numerals indicate like parts throughout the several views, FIGS. 1-6 depict various views of a fluid transfer device accessory 100 that is detachable to a fluid transfer device of a fluid transfer assembly.

More particularly, a detachable fluid transfer device accessory 100 may comprise a body 102 comprising an upper extension 104 defining a lower engagement surface 106, a lower extension 108 defining an upwardly extending protrusion 110, and a connector portion 112 extending between the upper extension 104 and the lower extension 108. For example, and as illustrated in the figures, the body 102 is integrally formed with the upper extension 104, the lower extension 108, and the connector portion 112 and is configured to define a cavity 114 therein. In some aspects, the body 102 is molded from a glass-filled polymer or other substantially rigid material, although other such manufacturing processes and materials are also contemplated.

Figure 3:
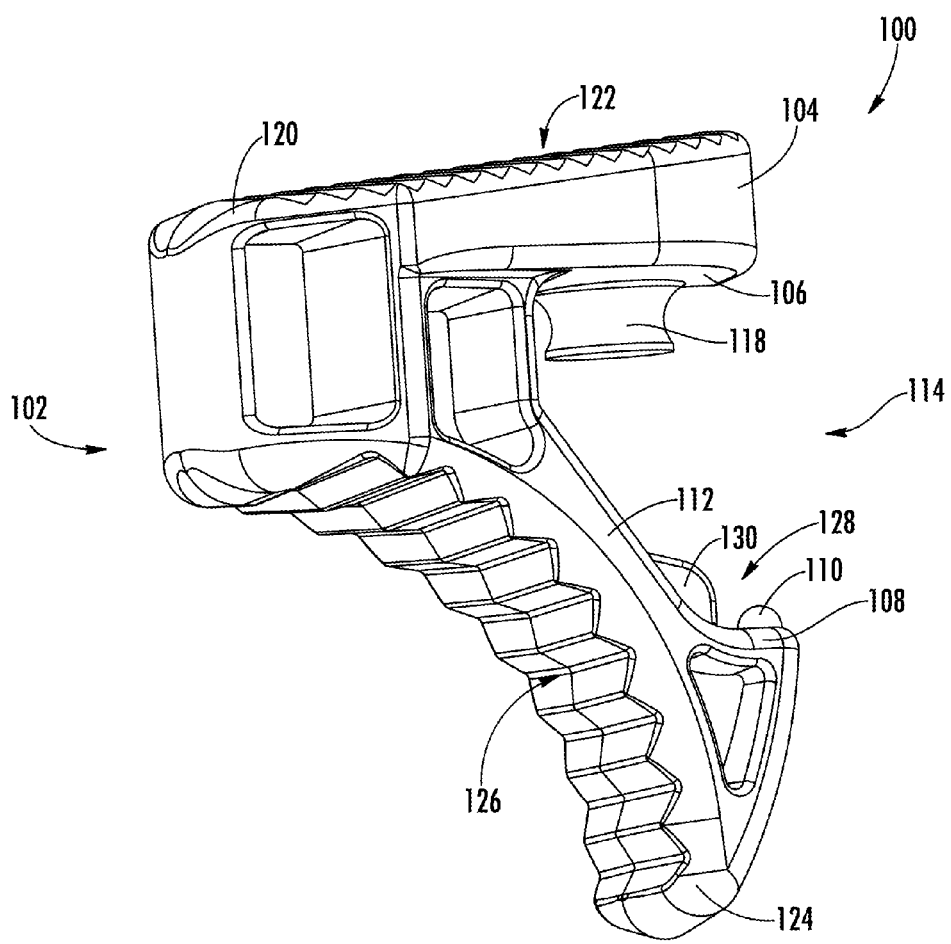
FIG. 3 is a side perspective view of the fluid transfer device accessory of FIG. 1.
Figure 4:
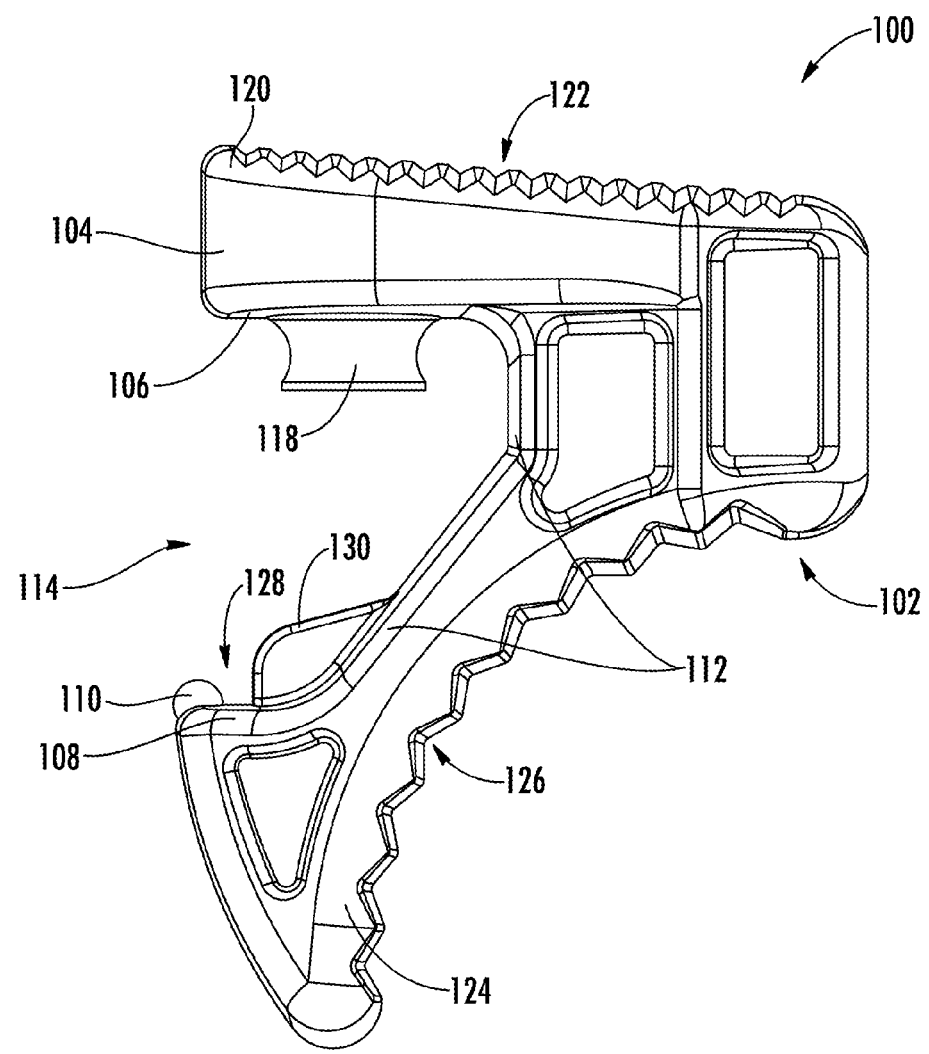
FIG. 4 is a side view of the fluid transfer device accessory of FIG. 1.
Figure 5:
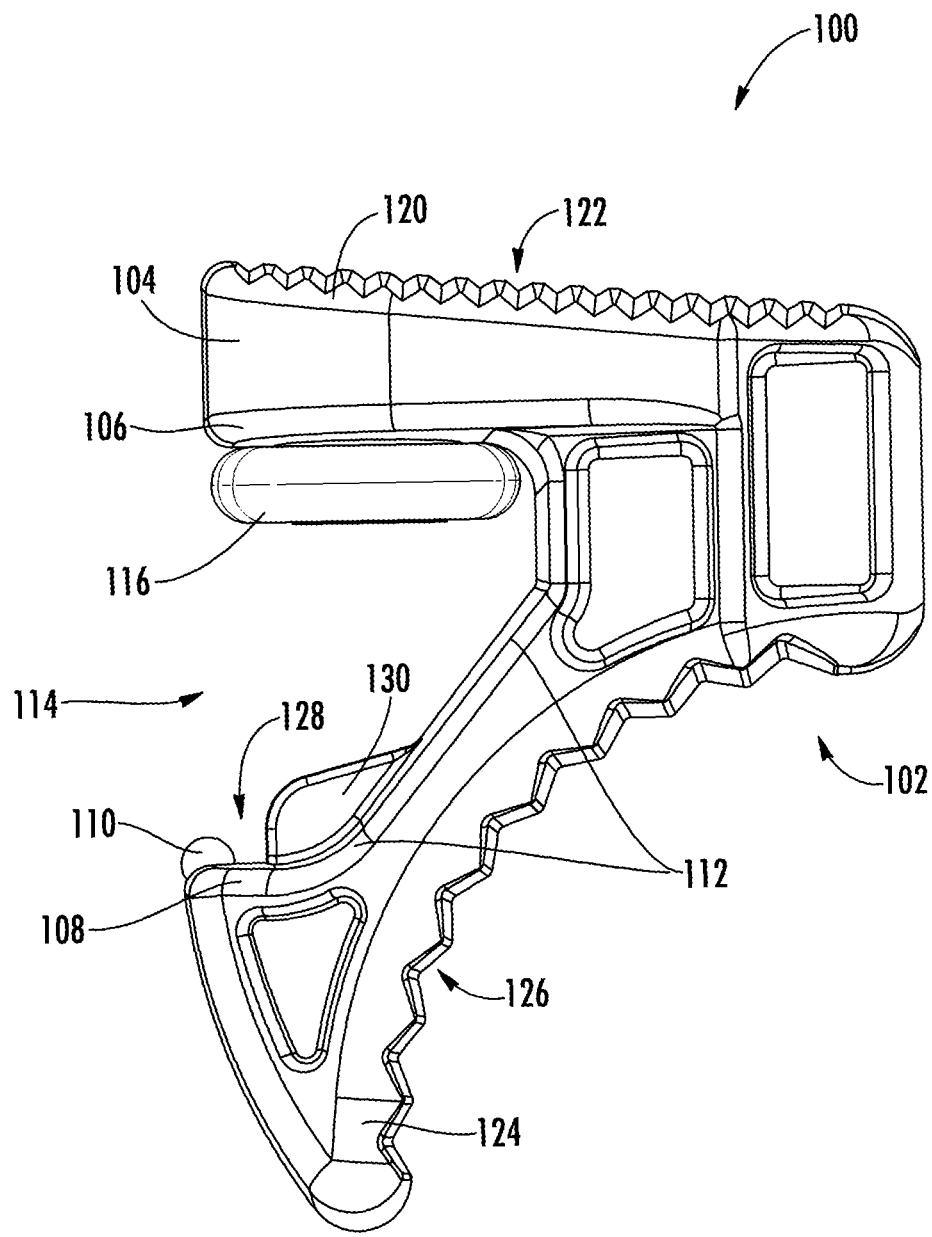
FIG. 5 is a side view of the fluid transfer device accessory of FIG. 1 including an O-ring.

In some aspects, the body 102 further comprises a resilient engagement member 116 coupled to the lower engagement surface 106 of the body 102. More particularly, in some aspects, the resilient engagement member 116 may comprise an O-ring as illustrated in FIG. 5. In such aspects, the lower engagement surface 106 of the upper extension 104 may define a post 118 configured to receive the engagement member or O-ring 116 thereon, as illustrated in FIGS. 3 and 4. In some aspects, a height of the O-ring 116 is greater than a height of the post 118. Otherwise, the height of the O-ring 116 and the post 118 are substantially the same or similar. The O-ring may be comprised of a resilient material capable of elastic deformation such as silicone, fluorosilicone, phenyl silicone, perfluoropolyether (PFPE), ethylene propylene diene monomer (EPDM), FKM, thermoplastic elastomer (TPE), thermoplastic polyurethane (TPU), organic rubber, polyurethane, and the like. In other alternative aspects, the resilient engagement member 116 may be another type of resilient member such as a spring. Regardless, the resilient engagement member 116 may be combined with the post 118 and/or the body 102 by overmolding or any other similar manufacturing process.

Figure 6:
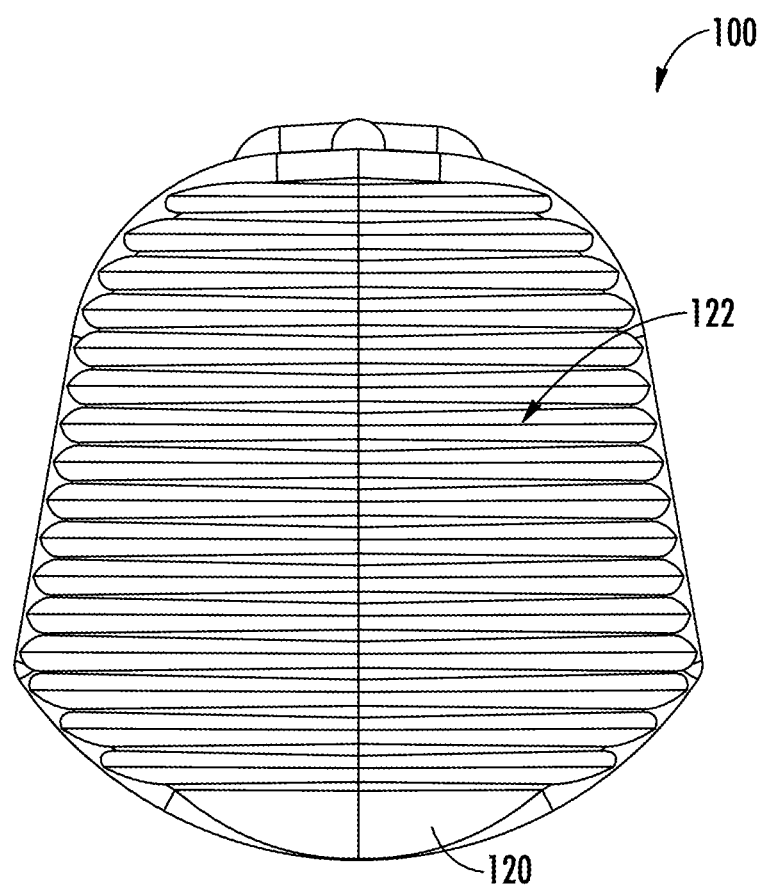
FIG. 6 is a top view of the fluid transfer device accessory of FIG. 1.

In some aspects, an upper surface 120 of the upper extension 104 defines a plurality of ridges 122 (FIG. 6). The upper surface 120 of the upper extension 104 may be configured as a gripping surface of the device accessory 100. As such, the plurality of ridges 122 may be provided as an anti-slip or enhanced gripping feature that enables a user to more comfortably and easily detach and reattach the device accessory 100 to a fluid transfer device. In this manner, the plurality of ridges 122 may be configured to span an entirety or a substantial entirety of the upper surface 120.

In some additional aspects, an outer surface 124 of the connector portion 112 opposite from the cavity 114 is concave. FIGS. 3-5 illustrate a side view of the device 100 to particularly show the concavity of the outer surface 124. The outer surface 124 of the connector portion 112 may be concave in order to aid in grasping the connector portion 112 when dexterity is limited (e.g., with gloved hands). Similar to the upper surface 120, the outer surface 124 may also define a plurality of ridges 126. The outer surface 124 may be configured as a gripping surface of the device accessory 100 so that the plurality of ridges 126 also serve to enable a user to more comfortably and easily detach and reattach the device accessory 100 to a fluid transfer device. In this manner, the plurality of ridges 126 may be configured to span an entirety or a substantial entirety of the outer surface 124.

Further, the lower extension 108 of the body 102 may define a slot 128 between the protrusion 110 and a rib 130 extending from one or both of the lower extension 108 and the connector portion 112 of the body 102. In some aspects, the slot 128 and rib 130 are provided to aid in appropriately aligning the accessory 100 with the fluid transfer device. For example, and as described herein, the protrusion 110 may be aligned within a corresponding component of a fluid transfer device (e.g., slot 212, FIG. 8).

Other components, elements, dimensions, and/or materials are also contemplated for the detachable fluid transfer device accessory 100 that may depend on the type of fluid transfer device to which the accessory 100 is engaged. More particularly, an exemplary fluid transfer device is described in U.S. Pat. No. 8,613,422 to Zumbrum, the entirety of which is incorporated by reference herein.

Figure 7:
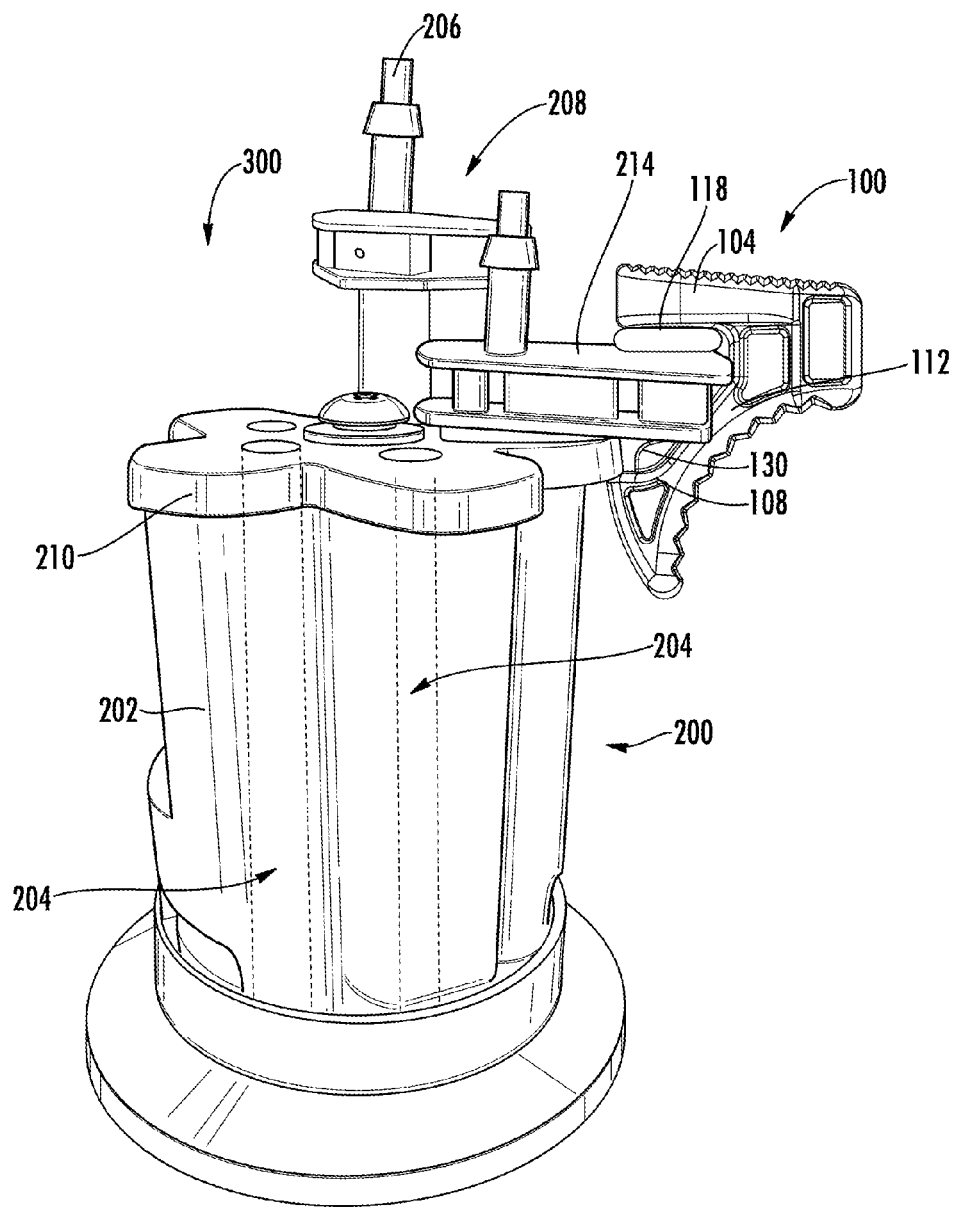
FIG. 7 is a top perspective view of a fluid transfer assembly comprising a fluid transfer device and a detachable fluid transfer device accessory.
Figure 8:
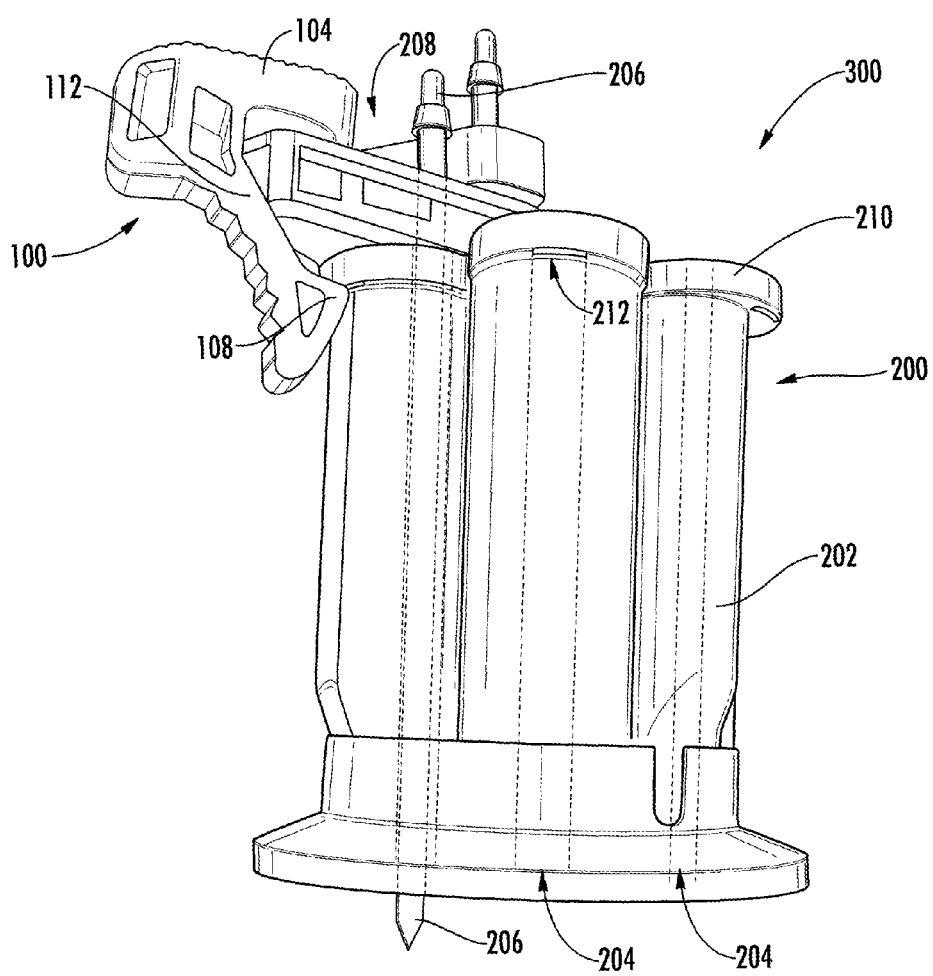
FIG. 8 is a side perspective view of a fluid transfer assembly comprising a fluid transfer device and a detachable fluid transfer device accessory.

In some other aspects, an exemplary fluid transfer device 200 of a fluid transfer assembly 300 is illustrated in illustrated FIGS. 7-8. The fluid transfer device 200 may comprise a housing 202. The housing 202 may include a body defining a plurality of chambers or passages 204 extending through the body from a proximal end to a distal end. For example, the body may have five passages 204 extending therethrough. A longitudinally displaceable cannula 206 may be disposed in and extend along each of the one or more elongate chambers 204 in the body. A septum sealing each of the chambers 204 may be at a first location; the septum being pierceable and self-sealing. In some aspects, a diaphragm sealing each of the chambers 204 may be at a second location intermediate the septum and the distal end of the chamber 204. Each cannula 206 may extend through and may be secured to the diaphragm and may have a sharpened end disposed adjacent to or in the septum. Longitudinal displacement of each cannula 206 may cause its sharpened end to pierce and project through the septum, the diaphragm stretching to accommodate the displacement of the cannula while maintaining its aseptic seal of the chamber 204. For example, a tab assembly 208 may be connected with each cannula 206 to control the displacement of the cannula 206 through its respective chamber 204. In such an example, each of the tab assemblies 208 is moveable with respect to the housing 202 between an extended configuration and a depressed configuration, the depressed configuration allowing flow of a fluid through the fluid transfer device 200. Alternatively, a fluid transfer device 200 may comprise other components, elements, dimensions, and/or materials.

In some aspects, the fluid transfer device 200 may be engageable with flexible tubing or other connective members at a distal end of each chamber 204 for attaching the chambers of the fluid transfer device 200 to sample containers. The fluid transfer device 200 may thus be used, for example, to take multiple fluid samples from a fluid receptacle, such as a tank, wherein a process is running. The samples may be taken simultaneously or over differing time intervals via the one or more chambers of the fluid transfer device 200.

However, in some aspects, one or more of the chambers 204 of the fluid transfer device 200 may not be needed during fluid transfer. For example, where the fluid transfer device 200 has five chambers 204 and only one of the chambers is needed for fluid transfer, a mechanism for temporarily fixedly displacing the corresponding cannula 206 is needed. Accordingly, the detachable fluid transfer device accessory 100 may be temporarily fixedly engaged with the tab assembly 208 to longitudinally displace the cannula 206 and retain the tab assembly 208 in a depressed configuration relative to the housing 202, and thus, retain the chamber 204 in an open chamber configuration for fluid transfer.

More particularly, FIGS. 7 and 8 illustrate the device accessory 100 engaged with the device 200. In some instances, the device 100 is releasably clamped to the device 200, such that the cavity 114 of the device accessory 100 is configured to receive a first tab assembly 208 of the fluid transfer device 200. A second tab assembly 208 of the fluid transfer device is also provided, however, this second tab assembly 208 is not received within a device accessory 100. The cavity 114 of the device 100 is sized to correspond to a width of the first tab assembly 208. Likewise, FIGS. 7 and 8 illustrate the upwardly extending protrusion 110 being configured to engage the housing 202 of the fluid transfer device 200. Particularly, the housing 202 may comprise a retaining cap 210 that defines a recess 212 such that the upwardly extending protrusion 110 is configured to engage the recess 212 in the retaining cap 210 (FIG. 8).

Further, FIGS. 7 and 8 illustrate the resilient engagement member 114 being configured to engage an upper surface 214 of the first tab assembly 208 to retain the first tab assembly 208 in a fixed or depressed configuration (i.e., open chamber configuration) relative to the housing 202. By comparison, the second tab assembly 208 remains in a fixed configuration (i.e., closed chamber configuration) relative to the housing 202), such that the corresponding cannula is not longitudinally displaced. However, the device accessory 100 may be completely detached or decoupled from the fluid transfer device 200 upon application of upward pressure on the lower extension 108, which will release the first tab assembly 208 from the depressed configuration and return the cannula to its original, non-displaced disposition.

As such, the fluid transfer device accessories, devices, and/or assemblies described herein may comprise any manner of fluid transfer device having any number of chambers, where such chambers may be individually retained in an open position by the fluid transfer device accessory(s) as opposed to mechanically isolating an individual chamber (e.g., by rotation, obstruction, etc.) Any structural configuration of a fluid transfer device accessory that is capable of individually retaining one or more chambers of a fluid transfer device in an open configuration is contemplated by this disclosure and shown by the numerous exemplary embodiments provided herein.

The fluid transfer device accessories and fluid transfer assemblies disclosed herein are low cost but still capable of effectuating a substantially aseptic seal to a vessel while still allowing maximum flexibility. The fluid transfer device accessories and assemblies disclosed herein may be assembled and then the entire devices or components thereof may be rendered substantially aseptic by, for example, gamma radiation. Alternatively, the entire device accessories, assemblies, and/or components thereof may be rendered substantially aseptic by exposure to steam above 121° C. for a period of time long enough to eliminate microorganisms. The entire device accessories, assemblies, and/or components thereof may also be rendered aseptic by chemical treatment, such as with ethylene oxide (ETO). Once rendered substantially aseptic, the fluid transfer device accessories, assemblies, and/or components may be appropriately packaged and stored to maintain the substantially aseptic state until ready for use.

The aforementioned fluid transfer device accessories and assemblies are particularly useful when the vessel from which fluid is being transferred is a stainless steel vessel. However, the aforementioned fluid transfer device accessories and assemblies are also useful when the vessel from which fluid is being transferred is a bioreactor bag. Such fluid transfer device accessories and assemblies, combined with a bioreactor bag, may be used in single-use bioreactors, such as the BIOSTAT® STR available from Sartorius. Fluid conduits may be sized to accommodate high density cell culture applications and provide a sterile, low-cost manner of collecting samples from bioreactor bags without the risk of leakage. As discussed above, the fluid transfer device accessories and assemblies provided herein may be connected to a variety of sample vessels or additional fluid transfer assemblies.

The fluid transfer device accessories and assemblies as well as a primary vessel (such as the stainless steel vessel, may be rendered substantially aseptic by any methods described above or others known in the art. Once rendered aseptic, the entire fluid transfer device accessories and assemblies may be aseptically packaged and distributed for use. An end user may open and utilize a completely closed and substantially aseptic system without risk of leaks due to the barbed or luer connectors extending from a bioreactor vessel. The foregoing descriptions of fluid transfer device accessories and assemblies illustrate and describe various embodiments. As various changes can be made in the above embodiments without departing from the scope of the invention disclosed and claimed herein, it is intended that all matter contained in the above description or shown in the accompanying figures shall be interpreted as illustrative and not limiting. Furthermore, the scope of the invention covers various modifications, combinations, alterations, etc., of the above-described embodiments that all are within the scope of the claims. Additionally, the disclosure shows and describes only selected embodiments of the invention, but the invention is capable of use in various other combinations, modifications, and environments and is capable of changes or modifications within the scope of the inventive concept as expressed herein, commensurate with the above teachings, and/or within the skill or knowledge of artisans in the relevant art. Furthermore, certain features and characteristics of each embodiment may be selectively interchanged and applied to other illustrated and non-illustrated embodiments of the invention without departing from the scope of the invention.

The invention claimed is:

1. A detachable fluid transfer device accessory, comprising:
   a body, comprising:
      an upper extension defining a lower engagement surface;
      a lower extension defining an upwardly extending protrusion; and
      a connector portion extending between the upper extension and the lower extension; and
   a resilient engagement member coupled to the lower engagement surface of the body,
   the upper extension, the lower extension, and the connector portion collectively defining a cavity configured to receive a tab assembly of a fluid transfer device,
   the upwardly extending protrusion being configured to engage a housing of the fluid transfer device,
   the resilient engagement member being configured to engage an upper surface of the tab assembly to retain the tab assembly in a fixed configuration relative to the housing.

2. The detachable fluid transfer device accessory of claim 1, wherein an upper surface of the upper extension defines a plurality of ridges.

3. The detachable fluid transfer device accessory of claim 1, wherein an outer surface of the connector portion opposite from the cavity is concave.

4. The detachable fluid transfer device accessory of claim 3, wherein the outer surface of the connector portion of the body defines a plurality of ridges.

5. The detachable fluid transfer device accessory of claim 1, wherein the lower extension of the body defines a slot.

6. The detachable fluid transfer device accessory of claim 5, wherein the slot is defined between the protrusion and a rib extending from one or both of the lower extension and the connector portion of the body.

7. The detachable fluid transfer device accessory of claim 1, wherein the resilient engagement member comprises an O-ring.

8. The detachable fluid transfer device accessory of claim 7, wherein the lower engagement surface of the upper extension defines a post configured to receive the O-ring thereon.

9. The detachable fluid transfer device accessory of claim 8, wherein a height of the O-ring is greater than a height of the post.

10. The detachable fluid transfer device accessory of claim 1, wherein the body comprises a substantially rigid material.

11. A fluid transfer assembly, comprising:
    a fluid transfer device, comprising:
       a plurality of tab assemblies;
       a housing defining a plurality of chambers respectively receiving one of the tab assemblies,
       each of the tab assemblies being moveable with respect to the housing between an extended configuration and a depressed configuration, the depressed configuration allowing flow of a fluid through the fluid transfer device; and
    a detachable fluid transfer device accessory configured to releasably clamp one of the tab assemblies and the housing to retain the one of the tab assemblies in the depressed configuration.

12. The fluid transfer assembly of claim 11, wherein the detachable fluid transfer device accessory comprises a body and a resilient engagement member coupled thereto,
    the resilient engagement member being configured to engage an upper surface of the one of the tab assemblies,
    the body being configured to engage the housing.

13. The fluid transfer assembly of claim 12, wherein the body comprises an upwardly extending protrusion configured to engage the housing.

14. The fluid transfer assembly of claim 13, wherein the housing comprises a retaining cap defining a recess and the upwardly extending protrusion is configured to engage the recess in the retaining cap.

15. The fluid transfer assembly of claim 12, wherein the body comprises:
    an upper extension defining a lower engagement surface coupled to the resilient engagement member;
    a lower extension defining an upwardly extending protrusion; and
    a connector portion extending between the upper extension and the lower extension.

16. The fluid transfer assembly of claim 15, wherein the upper extension, the lower extension, and the connector portion collectively define a cavity configured to receive the one of the tab assemblies of the fluid transfer device.

17. The fluid transfer assembly of claim 16, wherein an outer surface of the connector portion opposite from the cavity is concave.

18. The fluid transfer assembly of claim 15, wherein an upper surface of the upper extension defines a plurality of ridges.

19. The fluid transfer assembly of claim 15, wherein the outer surface of the connector portion of the body defines a plurality of ridges.

20. The fluid transfer assembly of claim 11, wherein the detachable fluid transfer device accessory is configured to completely decouple from fluid transfer device.

* * * * *